US006581410B1

United States Patent
Johnson et al.

(10) Patent No.: US 6,581,410 B1
(45) Date of Patent: Jun. 24, 2003

(54) LOW TEMPERATURE SEPARATION OF HYDROCARBON GAS

(75) Inventors: Grant L. Johnson, Manchester (GB); Adrian J. Finn, Manchester (GB); Terence R. Tomlinson, Manchester (GB)

(73) Assignee: Costain Oil Gas & Process Limited, Manchester (GB)

( * ) Notice: Subject to any disclaimer, the term of this patent is extended or adjusted under 35 U.S.C. 154(b) by 0 days.

(21) Appl. No.: 09/857,598

(22) PCT Filed: Dec. 8, 1999

(86) PCT No.: PCT/GB99/04117

§ 371 (c)(1),
(2), (4) Date: Sep. 4, 2001

(87) PCT Pub. No.: WO00/34213

PCT Pub. Date: Jun. 15, 2000

(30) Foreign Application Priority Data

Dec. 8, 1998 (GB) ............................................. 9826999

(51) Int. Cl.$^7$ ................................................. F25J 3/00
(52) U.S. Cl. ........................................ 62/621; 62/631
(58) Field of Search ........................... 62/630, 631, 621

(56) References Cited

U.S. PATENT DOCUMENTS

| | | | | | |
|---|---|---|---|---|---|
| 2,600,494 A | * | 6/1952 | Ferro, Jr. ..................... | 62/631 |
| 3,313,724 A | * | 4/1967 | Kniel ............................ | 62/631 |
| 4,456,461 A | * | 6/1984 | Perez ........................... | 62/630 |
| 4,617,039 A | | 10/1986 | Buck ............................. | 62/26 |
| 4,690,702 A | | 9/1987 | Paradowski et al. ........... | 62/23 |

FOREIGN PATENT DOCUMENTS

WO    WO 00/34213    6/2000

* cited by examiner

Primary Examiner—Ronald Capossela
(74) Attorney, Agent, or Firm—Marshall, Gerstein & Borun

(57) ABSTRACT

The invention provides a process for the separation of a heavier hydrocarbon fraction from a gaseous feed comprising a mixture of hydrocarbons, which process comprises subjecting the feed to a first fractionation to form a condensed product; subjecting the condensed product to a second fractionation, at a lower pressure than the first fractionation pressure, to provide the heavier hydrocarbon fraction and distillate fraction; and withdrawing the produced heavier fraction wherein the distillate from the second fractionation is partially condensed to provide reflux streams for both the first and second fractionations. Running the second fractionation at a lower pressure than the first means that there is phased let-down of pressure in two stages, leading to an increased pressure at the suction of the residue gas compressor and reduces power consumption. It also allows more efficient performance of the heat exchanger used to partially condense the reflux streams and simplifies the process, affording opportunities to better integrate process cooling and warming streams so increasing process efficiency. Increasing process efficiency reduces process power requirements or increases recovery of the desired heavier hydrocarbons or realizes both of these effects.

15 Claims, 1 Drawing Sheet

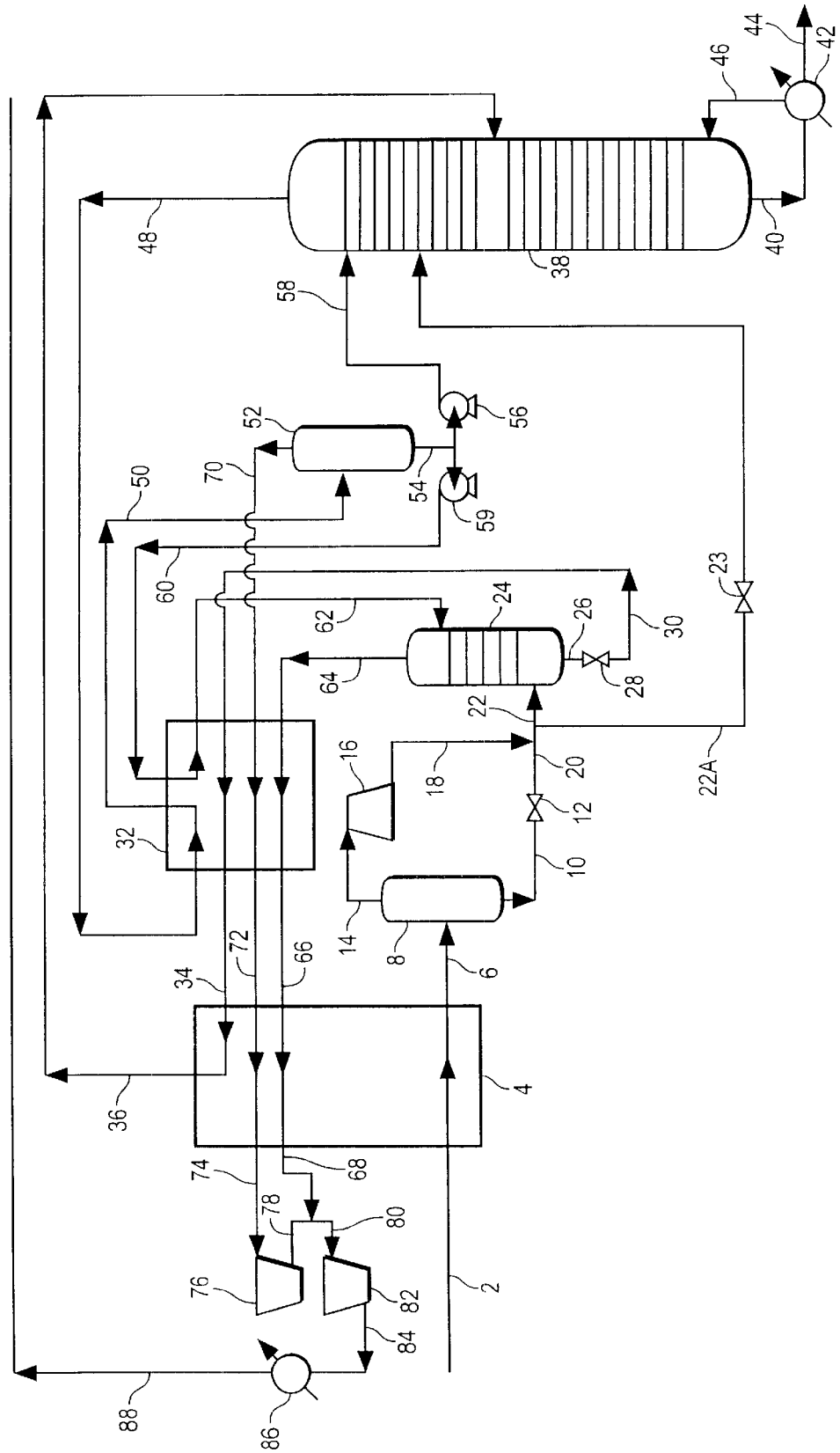

LOW TEMPERATURE SEPARATION OF HYDROCARBON GAS

This is the U.S. national phase of International Application No. PCT/GB99/04117 filed Dec. 8, 1999, the entire disclosure of which is incorporated herein by reference.

This invention relates to processes, and to apparatus for effecting such processes, for the cryogenic fractionation of gaseous feeds comprising mixtures of hydrocarbons.

Conventional processes which seek to effect very high recovery of propane and heavier components from natural gas typically utilise a combination of heat exchange, turbo-expansion and phase separation steps. The use of turbo-expansion produces work which can be used to improve overall process performance and, by removing energy from the feed gas, lowers its temperature. The feed gas is partially condensed to give a liquid stream, enriched in the valuable, heavier components being recovered and a vapour stream which may undergo further partial condensation steps. These partial condensation steps result finally in one or more liquid streams and a first residue vapour stream. The liquid streams are fed to a deethaniser column which removes the majority of the ethane and lighter components, producing a stable liquid stream and a second residue vapour stream.

Traditionally, to provide deethaniser column reflux, the top feed to the column has been the stream resulting from work expansion of the vapour remaining after partial condensation. The liquid fraction of this stream acts as a reflux.

In these conventional processes, recovery of the valuable propane and heavier components is reduced by the losses of such components in the first residue vapour stream formed after partial condensation of the feed, and losses in the second residue vapour stream from the deethaniser. Increasing liquids recovery requires increased condensation of the feed, and/or improved deethaniser column performance, generally by reducing column pressure and expander exhaust pressure to reduce overheads temperature. Increasing the condensation of heavier components upstream of the deethaniser also increases the amount of lighter components condensed and passed to the deethaniser for removal. Very high liquids recoveries can result in uneconomically high power requirements in either recompression of the residual vapours to required product pressure or external refrigeration to increase liquids condensation or in feed gas compression which also increases liquids condensation. As high power results in high plant capital and operating costs, methods to reduce power requirement whilst maintaining low temperatures have previously been proposed.

It is known that the introduction of an absorption column, enabling contact of the vapour phase of the partially condensed feed with a light hydrocarbon reflux stream in a multistage operation, can selectively increase the recovery of heavy components, and give an advantage over a simple separator. For a given recovery, the liquid passed to the deethaniser will contain less light components, reducing the duty on the deethaniser and reducing vapour compression to required product pressure.

In the invention of U.S. Pat. No. 4,617,039, deethaniser column overhead vapours are partially condensed and the liquid formed is used to absorb heavy components from the expander outlet vapour in an absorption column. The liquid bottoms from this column are then pumped to the top of the deethaniser column to act as a reflux stream. By virtue of this arrangement, unless the deethaniser column overheads are boosted in pressure, the deethaniser column must operate at a higher pressure than the absorption column.

The use of absorption column bottoms gives a reflux stream which is subcooled and relatively rich in heavy components. Whilst this results in improved performance, the subcooled stream entering the deethaniser increases markedly in temperature upon entering the column which indicates reduced process efficiency.

In the invention of U.S. Pat. No. 4,690,702, a method is described for the cryogenic fractionation of a gaseous feed into a residual gas containing the most volatile compounds of the feed and into a liquid product containing the heaviest compounds of the feed. This method includes the use of a "purifying-refrigerating" column in which the vapour from the partial condensation of the gas is contacted with a liquid formed from the partial condensation of the overhead vapour stream from the deethaniser column, and/or by the liquid distillate. In this process, the liquid from the base of the "purifying-refrigerating" column is pumped to the deethaniser column to act as a feed. The deethaniser column must run at a higher pressure than the "purifying-refrigerating" column in order to produce a refrigeration effect on letting down in pressure the partially condensed distillate stream. By contacting the residual gas directly with cold liquid in the "purifying-refrigerating" column, refrigeration is transferred very effectively.

This invention seeks to provide an improved process in which heavier hydrocarbon fractions are more effectively separated from a gaseous feed comprising a mixture of hydrocarbons wherein overall process power requirements are reduced; or recovery of the desired heavier hydrocarbon fraction is increased to a high level; or both of these effects are realised.

According, therefore, to one aspect of this invention, there is provided a process for the separation of a heavier hydrocarbon fraction from a gaseous feed comprising a mixture of hydrocarbons, which process comprises subjecting the feed to a first fractionation to form a condensed product; subjecting the condensed product to a second fractionation, at a lower pressure than the first fractionation pressure, to provide the heavier hydrocarbon fraction and a distillate fraction; and withdrawing the produced heavier fraction wherein the distillate from the second fractionation is partially condensed to provide reflux streams for both the first and the second fractionations.

The present invention is described below with particular reference to the recovery of propane and heavier components from gaseous feeds comprising a mixture of hydrocarbons. However, the invention is also applicable to the recovery of components which may be heavier than propane. Furthermore, the invention is not limited to the recovery of paraffinic compounds but is also applicable to the recovery of olefinic compounds such as propylene.

Gaseous feeds from which valuable, heavier hydrocarbon fractions can be produced include natural gas, gases associated with petroleum refining and gases associated with petrochemical manufacture.

In the process of the present invention the gaseous feed comprising a mixture of hydrocarbons undergoes one or more heat exchange and work expansion, for example turbo-expansion, operations which lead to one or more partially condensed hydrocarbon streams which are subjected to one or more phase separation operations.

Thus, prior to the first fractionation, the gaseous feed may be cooled (for example, by mechanical refrigeration and/or by integrated multistream heat exchange) to form a partially condensed fluid feed. This may then suitably be subject to one or more first phase separations. Part of the feed gas cooling duty may be effected in an intermediate reboiler located at an intermediate position up the second, lower pressure fractionator. Again prior to the first fractionation, the so separated vapour phase may be subjected to an operation (for example, expansion through one or more turbo-expanders) which results in the phase becoming a two phase feed. Likewise, the so separated liquid phase may be subjected to an operation (for example, expansion across one or more valves) which results in it also becoming a two-phase feed. The two feeds may be recombined prior to being fed to the first fractionation (for example, in a high pressure wash column). In the alternative, a portion of a two-phase feed may, optionally after heat exchange, be fed directly to the second fractionation or the individual streams may be fed to separate points of the first fractionation.

The liquid produced in the first fractionation may then be subjected to one or more operations (for example, expansion across a valve and/or warming by one or a plurality of integrated multistream heat exchanges) to produce a two phase stream which is then subject to the second fractionation at lower pressure (for example, in a deethaniser). In the alternative, the liquid produced in the first fractionation may be fed directly to the second fractionation.

The overhead vapour from the deethaniser is at least partially condensed, and a portion of the liquid formed provides reflux to the top of the deethaniser column.

A further portion of the condensed deethaniser overheads may be subcooled in a well integrated heat exchange operation and pumped to an absorption column, here termed the wash column. This wash column, containing fractionation trays or packing, allows intimate contact of the reflux liquid with the vapours form the partial condensation of feed gas. Propane and heavier components which would otherwise remain uncovered in the residue vapour are absorbed into the liquid and overall recovery of the desired components and is therefore increased. The wash column operates at a higher pressure than the deethaniser column.

Thus, in accordance with an important aspect of this invention, the second fractionation is carried out at a lower pressure than the first fractionation. This phased let-down of pressure in two stages leads to an increased pressure at the suction of the residue gas compressor and reduces power consumption. It also allows more efficient performance of the heat exchanger used to partially condense the reflux streams.

This also simplifies the process and affords opportunities to better integrate process cooling and warming streams so increasing process efficiency. Increasing process efficiency reduces process power requirements or increases recovery of the desired heavier hydrocarbons or realises both of these effects.

The cooling duty for the described deethaniser overheads condenser, which provides reflux to both the deethaniser column and wash column, may generally be provided by efficient multistream heat exchange by evaporating all or part of the cold liquid leaving the wash column, and rewarming residue vapours from the wash column and the deethaniser reflux drum.

The rewarmed liquid from the wash column may then be fed to the deethaniser column at a midpoint, as a two phase stream. The location of the feed point is optimised to maximise process efficiency.

In accordance with an important aspect of this invention, the distillate from the second fractionation at a lower pressure than the first fractionation may be subjected to phase separation, the separated liquid phase exiting as a plurality of streams one or more of which is conveyed, suitably with pumping, to reflux the first fractionation, optionally after cooling, while the other is conveyed, suitably with pumping to reflux the second fractionation.

Thus a single condensed stream may be used to reflux both the first and second fractionation columns. According to an advantageous feature of the invention, the vapour stream resulting from the phase separation is not used as a reflux stream and is compressed and rewarmed to provide a residual gas product.

The vapour stream from the first, higher pressure fractionation may be compressed and cooled (for example, by cooling water or air at essentially ambient temperature) to give a valuable residue gas product. One or more of the turbo-expanders may drive at least one compressor for example a sales gas compressor, to reduce overall power consumption.

It is desirable that the heat exchangers may be combined in a fully integrated heat exchange system. Furthermore, the second fractionation may utilise one or more side heat exchangers.

This invention also provides apparatus for the separation of a heavier hydrocarbon fraction from a gaseous feed comprising a mixture of hydrocarbons, which apparatus comprises:
  a first fractionator;
  a second fractionator operable at a lower pressure than the first fractionator;
  means for veying condensed product from the first fractionator to the second fractionator;
  means for withdrawing distillate from the second fractionator, partially condensing the distillate and veying it, as a reflux stream, to both the first and second fractionators.

The invention will now be described, by way of Example, with reference to the accompanying drawing, in which:

The sole FIGURE represents a flow diagram of the process of the present invention. This specific description is illustrated by a process for high propane recovery; as will be clear from the description, however, the invention may be utilised in relation also to other gaseous hydrocarbon feeds.

The feed gas at an elevated pressure 2 is passed through heat exchange system 4 where it is partially condensed. The two phase stream 6 is passed to a vapour/liquid separator 8 where the liquid phase 10 is separated from the uncondensed vapour phase 14. The vapour 14 is work expanded in turbo-expander 16 to give a two phase stream 18. The liquid 10 is expanded across valve 12 to give a two phase stream 20. Streams 18 and 20 are combined to give a two phase stream 22 which is fed to the bottom of a high pressure wash column 24. A stream 22A carries a portion of the two-phase stream 22A, through a valve 23, directly to the deethaniser column 38, if desired.

Liquid 26 from the bottom of the high pressure wash column 24 is expanded across valve 28 and the resulting stream 30 is warmed in heat exchange system 32 to give stream 34 which is further warmed in heat exchange system 4 to give a two phase stream 36 which is fed at a midpoint of a deethaniser column 38. The liquid from the bottom of the deethaniser column 38 is fed to a reboiler 42 from which is drawing a vapour return 46 to the bottom of the deethaniser column 38 and a liquid product 44 containing the recovered heavy components of the feed gas which may then be conveyed to a fractionation train (not shown).

Reflux to the deethaniser column and the high pressure wash column is provided in the following manner. Vapour 48 from the top of the deethaniser column 38 is partially condensed in the heat exchange system 32 and conveyed, via line 50, to a vapour/liquid separator 52 in which a liquid stream 54 and a vapour stream 70 are separated. A portion of the liquid is elevated in pressure by pump 56 and this stream is passed to the top of the deethaniser column 38. The remainder of the liquid is elevated in pressure by pump 59 and this stream 60 is further sub-cooled in heat exchanger system 32 to give a sub-cooled liquid 62 which is passed to the top of the wash column 24. Through this arrangement the vapour phase of the high pressure wash column feed 22 is contacted with a sub-cooled liquid reflux stream.

The residual vapours are rewarmed and compressed in the following manner. Vapour 70 from vapour/liquid separator 52 is warmed in heat exchange system 32 giving gas 72 which is further warmed in heat exchange system 4 to give gas 74. Similarly, vapour 64 from the top of the high pressure wash column 24 is warmed in heat exchange system 32 giving gas 66 which is further warmed in heat exchange system 4 to give gas 68. Gas 74 from heat exchange system 4 is compressed in 1st stage compressor 76

The invention is now illustrated by the following Example.

EXAMPLE

A feed gas, having an initial composition as shown in the third column of the TABLE below, was treated in accordance with the process of the present invention in apparatus shown diagrammatically in the sole FIGURE. Stream numbers in the TABLE refer to the corresponding streams in the FIGURE.

It is found that there is a 96.9% recovery of propane and a 100% recovery of butane.

TABLE

| | | Stream | | | | | |
|---|---|---|---|---|---|---|---|
| | | 2 | 14 | 22 | | 64 | 70 |
| | | Description | | | | | |
| | | Feed Gas | Expander Inlet | Wash Column Bottom Feed | | Wash Column Vapour | Separator 12 Vapour |
| Vapour Fraction | (molar) | 1 | 1 | 0.8086 | Vapour Liquid | 1 | 1 |
| Temperature | (° C.) | 30.0 | −32.0 | −69.0 | −69.0 −69.0 | −74.0 | −52.3 |
| Pressure | (kPa(a)) | 7000 | 6820 | 2500 | 2500 2500 | 2500 | 1990 |
| Mass Flow | (kg/h) | 304494 | 238435 | 304494 | 211722 92772 | 219336 | 34737 |
| Molar Flow | | | | | | | |
| Nitrogen | (kgmole/h) | 90 | 86 | 90 | 88 2 | 88 | 2 |
| Carbon Dioxide | (kgmole/h) | 300 | 245 | 300 | 208 92 | 224 | 76 |
| Methane | (kgmole/h) | 12293 | 11086 | 12293 | 11177 1115 | 11128 | 1165 |
| Ethane | (kgmole/h) | 1350 | 966 | 1350 | 587 763 | 928 | 413 |
| Propane | (kgmole/h) | 600 | 298 | 600 | 64 536 | 13 | 5 |
| i-Butane | (kgmole/h) | 75 | 26 | 75 | 2 73 | 0 | 0 |
| n-Butane | (kgmole/h) | 150 | 42 | 150 | 3 147 | 0 | 0 |
| t-Pentane | (kgmole/h) | 45 | 8 | 45 | 0 45 | 0 | 0 |
| n-Pentane | (kgmole/h) | 45 | 6 | 45 | 0 45 | 0 | 0 |
| n-Hexane | (kgmole/h) | 30 | 2 | 30 | 0 30 | 0 | 0 |
| n-Heptane | (kgmole/h) | 15 | 0 | 15 | 0 15 | 0 | 0 |
| n-Octane | (kgmole/h) | 7 | 0 | 7 | 0 7 | 0 | 0 |
| Total: | (kgmole/h) | 15000 | 12765 | 15000 | 12130 2870 | 12381 | 1661 |

| | | Stream | | | | |
|---|---|---|---|---|---|---|
| | | 62 | 36 | | 44 | 88 |
| | | Description | | | | |
| | | Wash Column Top Feed | Death\after Column Feed | | MOL | Residual Gas |
| Vapour Fraction | (molar) | 0 | 0.7046 | Vapour Liquid | 0 | 1 |
| Temperature | (° C.) | −70.9 | 2.0 | 2.0 2.0 | 77.5 | 30.0 |
| Pressure | (kPa(a)) | 2500 | 2020 | 2020 2020 | 2010 | 7000 |
| Mass Flow | (kg/h) | 19885 | 105043 | 59873 45171 | 50419 | 254074 |
| Molar Flow | | | | | | |
| Nitrogen | (kgmole/h) | 0 | 2 | 2 0 | 0 | 90 |
| Carbon Dioxide | (kgmole/h) | 33 | 108 | 95 14 | 0 | 300 |
| Methane | (kgmole/h) | 143 | 1309 | 1232 77 | 0 | 12293 |
| Ethane | (kgmole/h) | 493 | 915 | 679 236 | 9 | 1341 |
| Propane | (kgmole/h) | 30 | 617 | 276 341 | 582 | 19 |
| i-Butane | (kgmole/h) | 0 | 75 | 19 56 | 75 | 0 |
| n-Butane | (kgmole/h) | 0 | 150 | 28 122 | 150 | 0 |
| t-Pentane | (kgmole/h) | 0 | 45 | 4 41 | 45 | 0 |
| n-Pentane | (kgmole/h) | 0 | 45 | 3 42 | 45 | 0 |
| n-Hexane | (kgmole/h) | 0 | 30 | 1 29 | 30 | 0 |
| n-Heptane | (kgmole/h) | 0 | 15 | 0 15 | 15 | 0 |
| n-Octane | (kgmole/h) | 0 | 7 | 0 7 | 7 | 0 | giving gas 78. Gas 78 is mixed with vapour 68 from heat exchange system 4 giving gas 80 which is compressed in 2nd stage compressor 82 to give gas 84 which is cooled in cooler 86 to give a residue gas product 88.

What is claimed is:
1. A process for separating a heavier hydrocarbon fraction from a gaseous feed comprising a mixture of hydrocarbons, which process comprises the steps of (a) subjecting the feed to a first fractionation to form a condensed product; (b) subjecting the condensed product to a second fractionation, at a lower pressure than the first fractionation pressure, to provide the heavier hydrocarbon fraction and a distillate fraction; (c) withdrawing the produced heavier fraction; and, (d) partially condensing the distillate from the second fractionation to provide reflux streams for both the first and second fractionations, said process being carried out at least in part under cryogenic conditions.

2. A process according to claim 1 comprising, prior to the first fractionation, cooling the gaseous feed to form a partially condensed fluid feed and subjecting the partially condensed fluid feed to phase separation to provide a separated vapour phase and a separated liquid phase.

3. A process according to claim 2 comprising, prior to the first fractionation, subjecting at least one of the separated vapour phase and the separated liquid phase to an operation which results in the or each phase becoming a two-phase feed.

4. A process according to claim 1 comprising, prior to the first fractionation step, feeding a portion of a two-phase feed directly to the second fractionation.

5. A process according to claim 1 comprising compressing and cooling the vapour stream from at least one of the first fractionation step and the second phase separation step to furnish a residue gas product.

6. A process according to claim 1 wherein step (d) is carried out in a heat exchanger and comprising rewarming at least part of the liquid separated from the partial condensation step in the heat exchanger.

7. A process according to claim 1 comprising cooling the distillate from the second fractionation step to form a partially condensed stream, separating the partially condensed stream into liquid and vapour streams, dividing the resulting liquid stream into first and second portions, and using the first and second portions as reflux streams for the first and second fractionations, respectively.

8. A process according to claim 7 comprising pumping and cooling the first stream prior to entering the first fractionation as a reflux stream.

9. A process according to claim 8 comprising pumping the second portion prior to entering the second fractionation as a reflux stream.

10. A process according to claim 7 comprising pumping the second portion prior to entering the second fractionation as a reflux stream.

11. A process according to claim 7 comprising rewarming and compressing the vapour stream to produce a residue gas product.

12. A process according to claim 7 wherein the first portion of the liquid stream is the sole reflux stream for the first fractionation step.

13. A process according to claim 7 wherein the second portion of the liquid stream is the sole reflux stream for the second fractionation step.

14. A process according to claim 7 wherein the reflux to the first fractionation column is free of liquid streams derived directly from said vapour stream.

15. Apparatus for separating a heavier hydrocarbon fraction from a gaseous feed comprising a mixture of hydrocarbons, which apparatus comprises:

a first fractionator;

a second fractionator operable at a lower pressure than the first fractionator;

means for conveying condensed product from the first fractionator to the second fractionator;

means for expanding the condensed product from the first fractionator prior to entry into the second fractionator; and, means for withdrawing distillate from the second fractionator, and partially condensing the distillate and conveying it, as a reflux stream, to both the first and second fractionators.

* * * * *

UNITED STATES PATENT AND TRADEMARK OFFICE
CERTIFICATE OF CORRECTION

PATENT NO. : 6,581,410 B1
DATED : June 24, 2003
INVENTOR(S) : Grant L. Johnson et al.

It is certified that error appears in the above-identified patent and that said Letters Patent is hereby corrected as shown below:

Column 5,
Lines 36 and 58, please change "t-Pentane" to -- i-Pentane --.

Column 6,
Line 24, please change "Separator 12 Vapour" to -- Separator 52 Vapour --.
Line 47, please change "Death/after Column Feed" to -- Deethaniser Column Feed --.
Line 47, please change "MOL" to -- NGL --.
Line 62, the last line of the chart was omitted. Please add a total line as follows:
-- Total:       (kgmole/h)     699    3318    2338    980    958    14043 --.

Signed and Sealed this

Seventeenth Day of August, 2004

JON W. DUDAS
*Acting Director of the United States Patent and Trademark Office*